US012642427B2

(12) United States Patent (10) Patent No.: US 12,642,427 B2
Kumar (45) Date of Patent: Jun. 2, 2026

(54) VIDEO LARYNGOSCOPE

(71) Applicant: Sujit Kumar, Redmond, WA (US)

(72) Inventor: Sujit Kumar, Redmond, WA (US)

( * ) Notice: Subject to any disclaimer, the term of this patent is extended or adjusted under 35 U.S.C. 154(b) by 0 days.

(21) Appl. No.: 18/908,183

(22) Filed: Oct. 7, 2024

(65) Prior Publication Data

US 2025/0113990 A1 Apr. 10, 2025

Related U.S. Application Data

(60) Provisional application No. 63/543,039, filed on Oct. 6, 2023.

(51) Int. Cl.
*A61B 1/267* (2006.01)
*A61B 1/00* (2006.01)
*A61B 1/06* (2006.01)

(52) U.S. Cl.
CPC ........ *A61B 1/267* (2013.01); *A61B 1/000094* (2022.02); *A61B 1/000095* (2022.02); *A61B 1/00016* (2013.01); *A61B 1/0002* (2013.01); *A61B 1/0004* (2022.02); *A61B 1/00048* (2013.01); *A61B 1/00052* (2013.01); *A61B 1/00055* (2013.01); *A61B 1/00147* (2013.01); *A61B 1/00163* (2013.01); *A61B 1/0661* (2013.01); *A61B 1/2673* (2013.01)

(58) Field of Classification Search
CPC ... A61B 1/00; A61B 1/00094; A61B 1/00011; A61B 1/0004; A61B 1/00016; A61B 1/0002; A61B 1/00163; A61B 1/267
See application file for complete search history.

(56) References Cited

U.S. PATENT DOCUMENTS

| | | | | |
|---|---|---|---|---|
| 2011/0130632 A1* | 6/2011 | McGrail | ............ | G02B 23/2446 |
| | | | | 600/188 |
| 2011/0196204 A1* | 8/2011 | Setty | ...................... | A61B 1/267 |
| | | | | 128/200.26 |
| 2016/0256047 A1* | 9/2016 | Newcomb | ............ | A61B 1/0684 |
| 2019/0133430 A1* | 5/2019 | Inglis | ................... | A61B 1/0005 |
| 2020/0367722 A1* | 11/2020 | Perez-Lizano | ..... | A61B 1/00073 |
| 2021/0315449 A1* | 10/2021 | Fakhim | .............. | A61B 1/00091 |
| 2022/0175231 A1* | 6/2022 | Ukrainksy | ........... | A61B 5/6821 |
| 2023/0397795 A1* | 12/2023 | Pilbeam | ................. | A61B 1/045 |

FOREIGN PATENT DOCUMENTS

WO WO-2012097181 A1 * 7/2012 ......... A61B 1/00052

* cited by examiner

*Primary Examiner* — Eduardo C Robert
*Assistant Examiner* — Holly Joanna Lane
(74) *Attorney, Agent, or Firm* — Vani Moodley, Esq.

(57) ABSTRACT

The present invention provides a video laryngoscope (100) to perform the intubation process. The video laryngoscope (100) includes a handle (10), a blade (20), a display unit (30), and an attachment assembly (25). The handle (10) includes a camera housing (16) with an image sensor (161) and a light source (162) arranged therein. The image sensor (161) is attached to the handle (10) through a camera channel (15) to visualise the path of the endotracheal tube. The camera housing (16) has a deflector (18) to avoid the blurry and distorted visuals generated due to the scattering of the light from the light source (162). The blade (20) is arranged on the handle (10) to cover the handle (10) and the camera channel (15). Further, the display unit (30) is provided for better visibility of the display screen (34) to visualise the path of the endotracheal tube.

11 Claims, 5 Drawing Sheets

181

18

1821a (1821)

1821b (1821)

182a(182)

182b(182)

1621

162

1682b(1682)

16

1682a(1682)

1611

161

16

1601

18

1611

1621

181

1602

VIDEO LARYNGOSCOPE

TECHNICAL FIELD

The present invention relates to a laryngoscopy device. More particularly, the present invention relates to a video laryngoscope.

BACKGROUND

A laryngoscope is a device, typically comprising a handle and a blade, which is used by clinicians during endotracheal intubation. The laryngoscope assists with intubation by allowing the clinician to visualise the path of the endotracheal tube as the laryngoscope passes through the glottis towards the trachea.

Intubation is the process of inserting a tube, called an endotracheal tube, through the mouth and then into the airway. Intubation is a necessary procedure performed before any surgery that requires a patient to be placed under general anesthesia. Intubation is also performed on patients who need to be placed on a ventilator to assist with breathing. The endotracheal tube is connected to either an anesthesia system or a ventilator, that pushes air into the lungs to deliver a breath to the patient. The laryngoscope is the device used for intubation.

Presently, traditional video laryngoscopes come in two form factors. In the first form factor, the display is detached from the handle and is attached to a cart. The display attached to the cart has a limited manoeuvrability. Also, the size of the display is 7-11 inches and the carts are bulky and hard to move around. While performing the intubation process, the clinician needs to look away from the patient and towards the display which is attached to the cart and not looking at the patient increases the risk of a failed process. In addition, cart-based systems tend to be more expensive and hospitals purchase a few units to be shared between multiple operating rooms. This results in the video laryngoscope not being available for every intubation procedure. In the second form factor, the display is attached to the handle but the displays are small, have poor image quality and are not manoeuvrable. Both form factors result in increased risk to the patient and repeated intubations.

Further, traditional video laryngoscope includes reusable blades that are used again and again for the intubation process. Repeated use of the blades leads to a higher risk of infection, increased operational burden on hospitals and high ownership costs.

Therefore, there is a need for a video laryngoscope, which overcomes few or all drawbacks of the prior art.

STATEMENT OF THE INVENTION

According to the present invention, there is provided with a video laryngoscope. The video laryngoscope may comprise a handle having an upper end and a lower end. the upper end may be adapted to receive a display unit, and the handle may be adapted to receive a blade for the intubation process. The video laryngoscope may further comprise a camera channel extending from the lower end of the handle. The camera channel may be a flexible link, with a first end connected to the handle and a second end comprising a camera housing. The camera housing may include an image sensor, arranged within the housing and facing outwardly to capture visuals of the path of an endotracheal tube, larynx, trachea, or airway. The camera housing may also include a light source arranged adjacent to the image sensor to illuminate the path of the endotracheal tube and the airway. Further, the camera housing may include a deflector mounted on the camera housing, positioned between the image sensor and the light source, to minimise light scatter and reduce direct light exposure to the image sensor.

Furthermore, the camera housing may be a rectangular box having a front portion and a back portion. The back portion may be configured to attach the camera housing to the camera channel, and the front portion may be adapted to accommodate the image sensor, the light source, and the deflector, all positioned outwardly to capture visuals of the path of the endotracheal tube, larynx, trachea, or airway.

The front portion of the camera housing may include an image sensor opening and a light source opening, adapted to expose the image sensor and the light source, respectively. These openings may allow the capturing of visuals of the path of the endotracheal tube, larynx, trachea, or airway.

The camera housing may have a first compartment and a second compartment arranged at the front portion. The first compartment may be adapted to receive and hold the image sensor facing outwardly through the image sensor opening, while the second compartment, arranged adjacent to the first, may be adapted to receive and hold the light source, facing outwardly through the light source opening.

The deflector may be a rectangular strip made of silicone material and may be attachable to the outer surface of the camera housing, positioned between the image sensor and the light source to minimize light scatter and direct light exposure to the image sensor.

The deflector may include a rectangular portion and a plurality of legs extending from the distal ends of the rectangular portion to mount the deflector on the camera housing.

The plurality of legs of the deflector may include respective locking elements. The camera housing may have a corresponding plurality of openings to receive the legs of the deflector, securing the deflector to the camera housing. The plurality of openings may be configured between the image sensor opening and the light source opening to receive the deflector and effectively separate the image sensor and the light source, minimizing light scatter and direct light exposure to the image sensor.

In another aspect, the deflector may be an extruded portion extending integrally from the outer surface of the camera housing. The extruded portion may extend in such a way that the image sensor opening and the light source opening are separated from each other to avoid direct light exposure to the image sensor from the light source.

Further, in the present invention, the blade of the video laryngoscope may be adapted to receive the camera channel and the camera housing within a cavity of the blade when attached to the handle.

The camera channel may be a flexible link extending from the tapered portion of the handle and may include an electric circuit configured to transfer visuals such as images and videos from the image sensor to the display unit.

The video laryngoscope may further include a camera channel that comprises a camera housing arranged at a distal end of the camera channel. The camera housing may include an image sensor and a light source arranged adjacent to each other, with a deflector mounted between the image sensor and the light source. The deflector may have a rectangular shape and a plurality of legs extending from the rectangular portion to mount the deflector on the camera housing. The plurality of legs may include locking elements to secure the deflector to corresponding openings in the camera housing.

An object of the present invention is to provide a video laryngoscope.

Another object of the present invention is to provide a video laryngoscope, which is adapted to control the infection rate in hospitals.

Yet another object of the present invention is to provide a video laryngoscope which is adapted to capture clear and non-distorted images of the path of the endotracheal tube, larynx, trachea or airway.

Still another object of the present invention is to provide a video laryngoscope which provides better visibility of the path of the endotracheal tube to the clinicians.

BRIEF DESCRIPTION OF THE DRAWINGS

Other features and advantages of the invention will become apparent when reading the detailed description given below, purely by way of example and in a non-limitative manner, referring to the following figures.

DETAILED DESCRIPTION

An embodiment of this invention, illustrating its features, will now be described in detail. The words "comprising, "having, "containing," and "including," and other forms thereof, are intended to be equivalent in meaning and be open ended in that an item or items following any one of these words is not meant to be an exhaustive listing of such item or items, or meant to be limited to only the listed item or items.

The present invention provides a video laryngoscope. The video laryngoscope is adapted to seamlessly attach and detach a display unit and a blade from a handle. The video laryngoscope is adapted to avoid the blurry and distorted visuals of the path of the endotracheal tube. Further, the video laryngoscope is adapted to control the infection rate which is spread due to the regular laryngoscopes. Furthermore, the video laryngoscope allows the clinicians to perform the intubation process without sacrificing the visibility of the display unit.

The terms "first," "second," and the like, herein do not denote any order, quantity, or importance, but rather are used to distinguish one element from another, and the terms "an" and "a" herein do not denote a limitation of quantity, but rather denote the presence of at least one of the referenced item. The disclosed embodiments are merely exemplary of the invention, which may be embodied in various forms.

Figure 1:
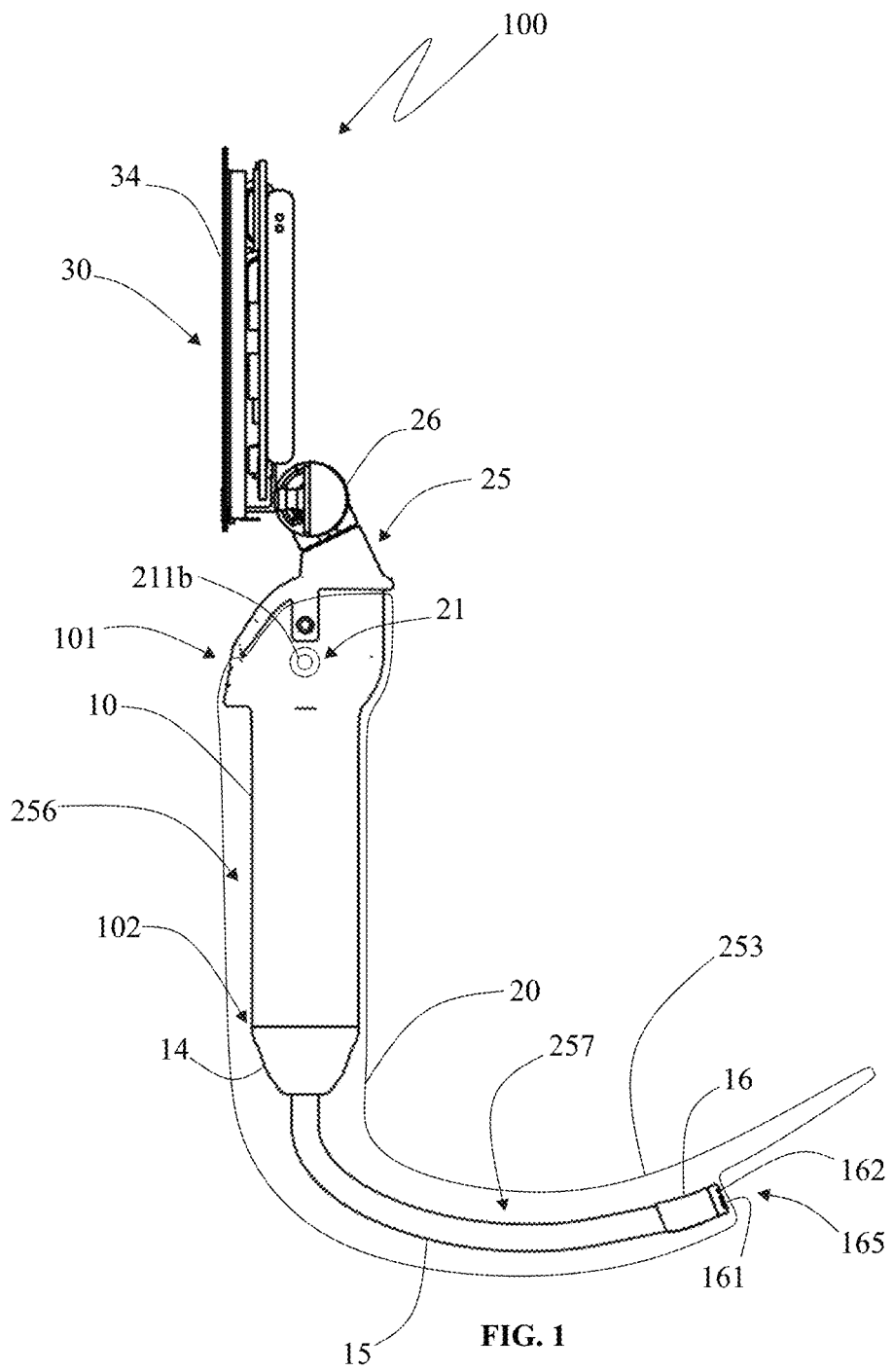
FIG. 1 illustrates a side view of a video laryngoscope in accordance with the present invention.
Figures 2, 3:
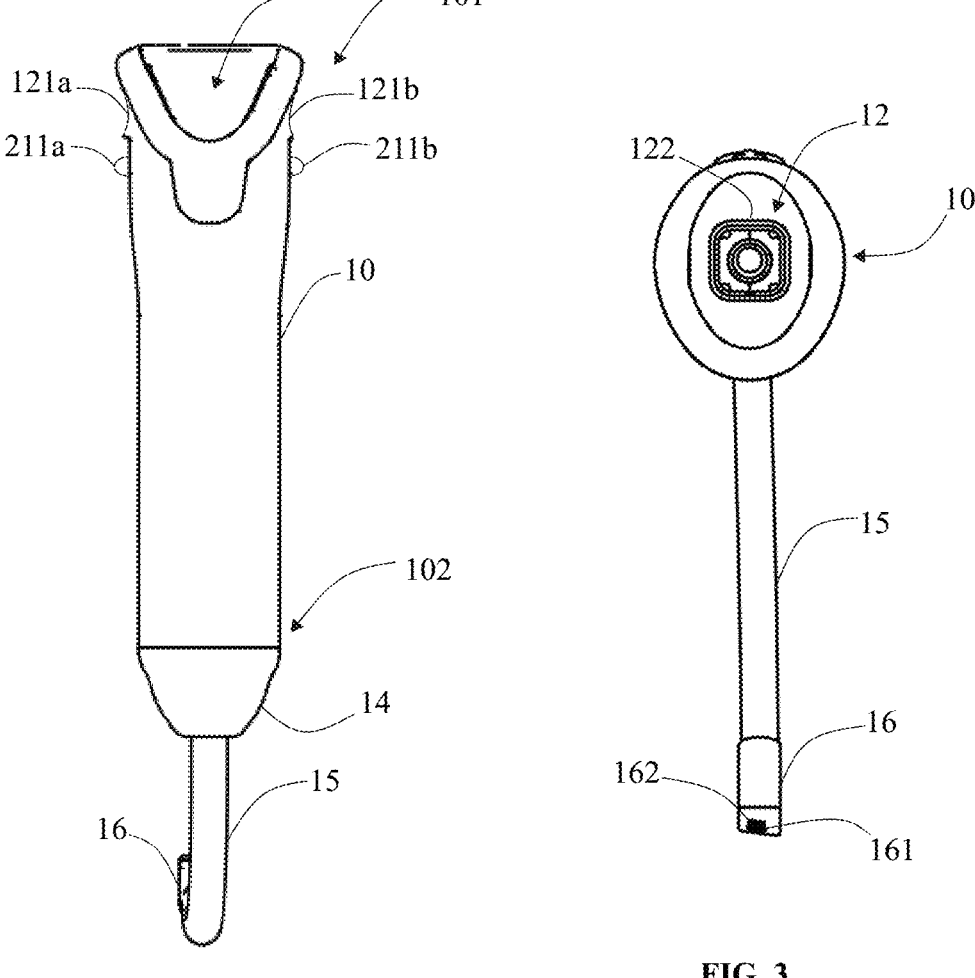
FIG. 2 illustrates a front view of a handle of the video laryngoscope in accordance with the present invention.
FIG. 3 illustrates a top view of the handle of the video laryngoscope in accordance with the present invention.

Referring now to FIGS. 1, 2, and 3, a video laryngoscope (100) in accordance with the present invention is illustrated. The video laryngoscope (100) includes a handle (10), a blade (20), a display unit (30), and an attachment assembly (25) to attach the display unit (30) to the handle (10). The handle (10) is an elongated member that has an ergonomic design that allows clinicians to easily hold the handle (10) during an intubation process. The handle (10) has an upper end (101) and a lower end (102). The upper end (101) of the handle (10) is provided with a receiving port (12) to receive the attachment assembly (25).

The lower end (102) of the handle (10) is provided with a tapered portion (14). Specifically, the lower end (102) of the handle (10) is provided with a camera channel (15) that extends from the tapered portion (14) of the handle (10). The camera channel (15) is a flexible link extending from the tapered portion (14) of the handle (10) and comprises an electric circuit to transfer the visuals like images and videos to the receiving port (12). Specifically, the camera channel (15) is electrically connected to a first terminal (122) of the receiving port (12). The camera channel (15) has a first end connected to the tapered portion (14) of the handle (10) and a second end comprising a camera housing (16). The camera housing (16) of the camera channel (15) is provided to capture visuals of the path of the endotracheal tube, larynx, trachea or airway.

Figures 4, 5, 6:
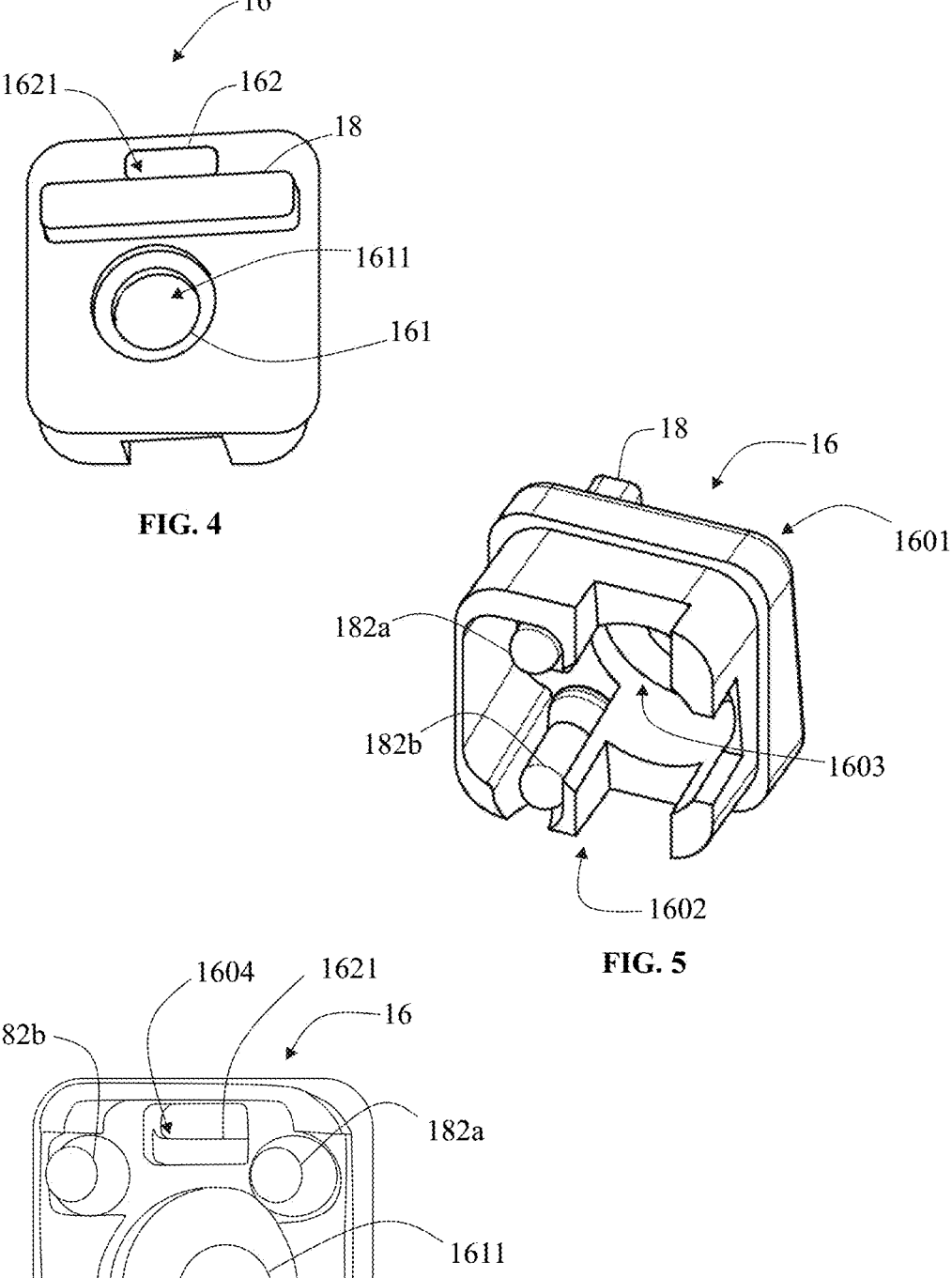
FIG. 4 illustrates a perspective view of a camera housing of the video laryngoscope in accordance with the present invention.
FIG. 5 illustrates a perspective view of an inner side of the camera housing of the video laryngoscope in accordance with the present invention.
FIG. 6 illustrates a back view of the camera housing showing openings provided in the camera housing.

Referring now to FIGS. 4, 5, and 6, the camera housing (16) includes an image sensor (161) and a light source (162). The image sensor (161) facilitates capturing of the visuals of the path of the endotracheal tube, larynx, trachea or airway and the light source (162) is configured to illuminate the path of the endotracheal tube and the airway. The light source (162) is arranged adjacent to the image sensor (161) within the camera housing (16). The image sensor (161) arranged within the camera housing (16) is facing outwardly to capture the visuals of the path of the endotracheal tube, larynx, trachea, or airway. Specifically, the camera housing (16) has an image sensor opening (1611) that allows the image sensor (161) to capture the visuals of the path of the endotracheal tube, larynx, trachea or airway. In the present aspect of the invention, the image sensor (161) is a 2-megapixel (MP) camera, but a person skilled in the art can use any other image sensor (161) having different specifications.

Further, the camera housing (16) includes a light source opening (1621) (as shown in FIGS. 4, and 6) to allow the light source (162) to illuminate the path of the endotracheal tube and the airway. In the present embodiment, the camera housing (16) is a rectangular box having a front portion (1601) and a back portion (1602). The back portion (1602) is configured to attach the camera housing (16) to the camera channel (15) and the front portion (1601) is adapted to accommodate the image sensor (161), the light source (162) and a deflector (18). The image sensor (161), the light source (162), and the deflector (18) are positioned to face outward from the camera housing (16) to capture visuals of the path of an endotracheal tube, larynx, trachea, or airway. Specifically, the front portion (1601) of the camera housing (16) has the image sensor opening (1611) and the light source opening (1621) adapted to expose the image sensor (161) and the light source (162) respectively.

Further, the camera housing (16) has a first compartment (1603) and a second compartment (1604) arranged at the front portion (1601) of the camera housing (16), specifically from internal side of the camera housing (16) corresponding to the image sensor opening (161) and the light source opening (1621) respectively. The first compartment (1603) is adapted to receive and hold the image sensor (161) within the housing (16) facing outward through the image sensor opening (1611) and the second compartment (1604) is arranged adjacent to the first compartment (1603) to receive and hold the light source (162) within the housing (16) facing outward through the light source opening (1604).

Furthermore, the deflector (18) is arranged on an outer surface of the camera housing (16) separating the image sensor opening (1611) and the light source opening (1621). The deflector (18) avoids the direct exposure of the light source (162) to the image sensor (161).

In the present aspect of the invention, the deflector (18) is a rectangular strip. The rectangular strip is made of silicone. A person skilled in the art can configure the deflector (18) with any other material, shape or size according to the size and position of the image sensor (161) and the light source (162). The deflector (18) is horizontally arranged between the light source opening (1621) and the image sensor opening (1611) to avoid the scattering of the light on the image sensor (161).

Figure 7:
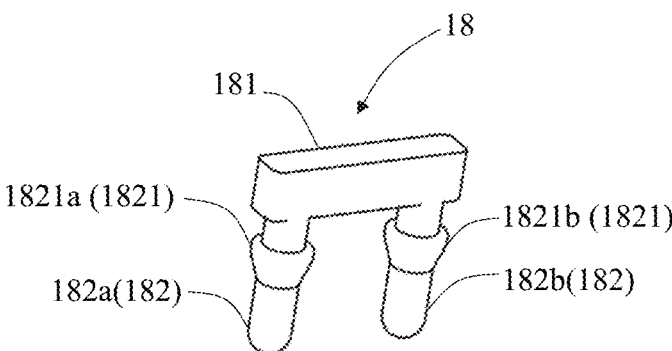
FIG. 7 illustrates a perspective view of a deflector of the video laryngoscope in accordance with the present invention.
Figure 8:
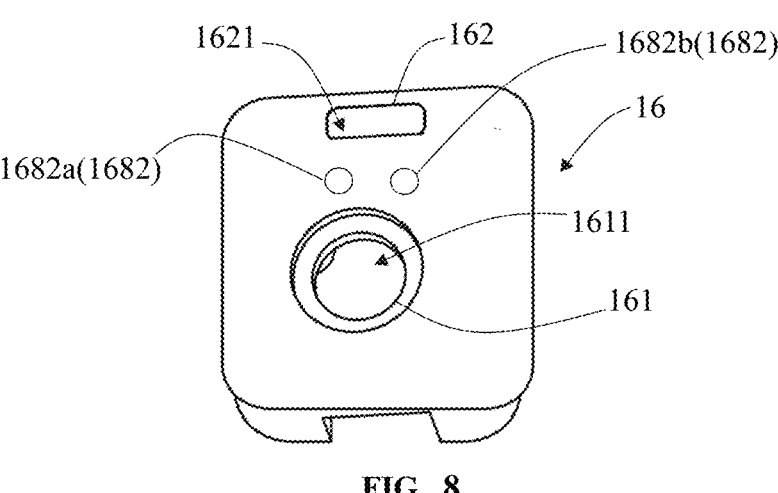
FIG. 8 illustrates a perspective view of the camera housing showing openings to receive the deflector shown in FIG. 7.

Referring now to FIGS. 7, and 8, the deflector (18) includes a rectangular portion (181), and a plurality of legs (182) extending from the rectangular portion (181). The plurality of legs (182) is provided with respective locking elements (1821) to attach the deflector (18) to the camera housing (16). Additionally, the camera housing (16) has a plurality of openings (1682) to receive the corresponding plurality of legs (182) of the deflector (18) to securely hold the deflector (18) on the camera housing (16). The plurality of openings (1682) is configured in between the image sensor opening (1611) and the light source opening (1682) to receive the deflector (18), separating the image sensor (161) and the light source (162) to minimise light scatter and direct light exposure to the image sensor (161).

In the present embodiment, the deflector (18) has two legs (182a, 182b) extending from distal ends of the rectangular portion (181). The two legs (182a, 182b) are provided with respective locking elements (1821a, 1821b) to attach the deflector (18) to the camera housing (16). Specifically, the camera housing (16) has two openings (1682a, 1682b) to receive the locking elements (1821a, 1821b) of the two legs (182a, 182b) to hold the deflector (18) on the outer surface of the camera housing (16). The deflector (18) is fixedly attached to the camera housing (16) using the locking elements (1821a, 1821b) but a person skilled in the art can provide the deflector (18) which is detachable from the camera housing (16). Specifically, the deflector (18) is detachable from the camera housing (16) if the deflector (18) has incurred damage or requires replacement.

Figure 9:
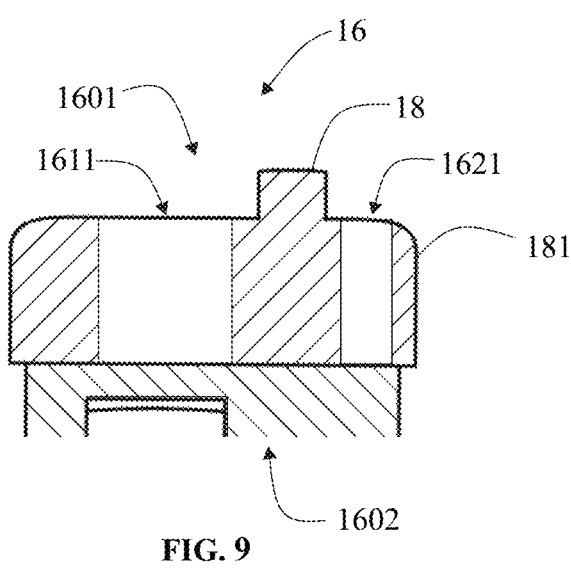
FIG. 9 illustrates a sectional view of a camera housing of the video laryngoscope in accordance with another embodiment.

In another embodiment shown in FIG. 9, the deflector (18) is an extruded portion that extends from the outer surface of the camera housing (16). The extruded portion is provided between the image sensor opening (1611) and the light source opening (1621) to avoid direct light exposure to the image sensor (161) from the light source (162). The scattering of the light from the light source (162) makes images distorted and blurry. The deflector (18) avoids direct exposure of the light source (162) to the image sensor (161) to avoid distortion and blurriness of the images.

In another aspect of the invention, the deflector (18) is a thin sheet (not shown) arranged between the image sensor opening (1611) and the light source opening (1621). The sheet can be made up of any material that absorbs light to avoid the direct exposure of the light source (162) on the image sensor (161).

Figure 10:
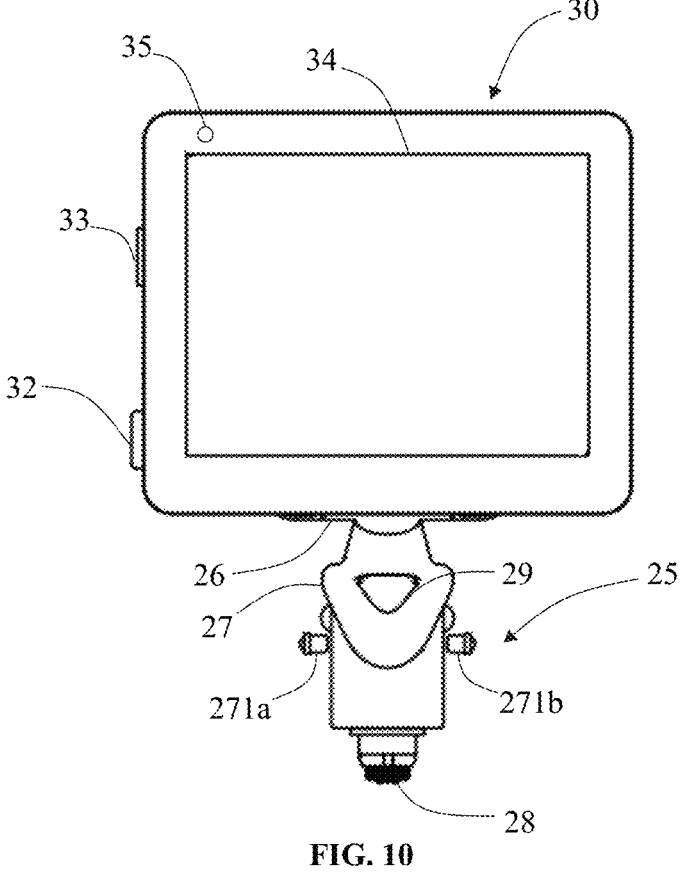
FIG. 10 illustrates a front view of a display assembly of the video laryngoscope in accordance with the present invention.

Referring now to FIGS. 1, and 10, the display unit (30) is provided which is attachable to the handle (10) through the attachment assembly (25). The attachment assembly (25) includes a housing (27), and a second terminal (28) which is electrically connected to the display unit (30). The housing (27) is connected to the display unit (30) using a hinge (26). The hinge (26) is provided to pivot the display unit (30) in a back-and-forth direction. The hinge (26) is connected to the display unit (30) and the housing (27). Specifically, the hinge (26) has a connecting element (not shown) that is adapted to attach to the housing (27). The housing (27) receives the connecting element of the hinge (26) to allow the display unit (30) to freely rotate around the central axis of the handle (10). The hinge (26) allows the display unit (30) to rotate in all the possible directions to configure the display unit (30) in a required position to provide better visibility to the clinician.

Further, the housing (27) includes two ball projections (271a, 271b) extending from an outer surface of the housing (27) and arranged opposite to each other to securely attach and detach the housing (27) to the handle (10). The two ball projections (271a, 271b) are biased to radially extend away from the centre axis of the housing (27). The housing (271a, 271b) is attached to the receiving port (12) of the handle (10). Specifically, the receiving port (12) has two openings (121a, 121b) to receive the respective ball projections (271a, 271b) of the housing (27) to securely hold the housing (27) within the receiving port (12) of the handle (10). The two ball projections (271a, 271b) ensure that the housing (27) is held in place until the two ball projections (271a, 271b) are pressed to detach the housing (27) of the attachment assembly (25). Specifically, the two ball projections (271a, 271b) have respective balls arranged at the extreme ends to easily press the two ball projections (271a, 271b) while detaching the housing (27) from the handle (10).

Once the display unit (30) is attached to the handle (10) through the attachment assembly (25), the second terminal (28) of the attachment assembly (25) electrically connects with the first terminal (122) of the receiving port (12) of the handle (10) to establish the electric connection between the camera channel (15) and the display unit (30). Specifically, upon attaching the attachment assembly (25) to the handle (10), the first terminal (122) and the second terminal (28) immediately establish an electric connection between the image sensor (161) and the display unit (30) enabling the instantaneous display of visuals of the path of the endotracheal tube, larynx, trachea, or airway on the display screen (34).

Furthermore, the attachment assembly (25) includes a record button (29) (as shown in FIG. 10) to capture an image or record a video. In the present aspect of the invention, the record button (29) is arranged on a portion of the housing (27). However, a person skilled in the art can arrange the record button (29) on any other portion in such a way that the clinician's thumb easily reaches to the record button (29) to capture an image or record a video.

Referring now to FIG. 10, the display unit (30) includes a battery (not shown), a power button (32), an output port (33), a display screen (34), a touch user interface (TUI) (not shown), a processor (not shown), and a memory (not shown) to store the visuals of the path of the endotracheal tube, larynx, trachea or airway. The battery is arranged within the display unit (30) to supply power to the display screen (34), the image sensor (161) and the light source (162) (shown in FIG. 4). The battery can be a replaceable battery or a rechargeable battery.

In another aspect of the invention, the handle (10) includes a battery (not shown) that can be used to supply power to the image sensor (161) and the light sensor (162) when the display unit (30) is not attached to the handle (10). In such case, the handle (10) establishes a wireless connection with the display unit (30) or an external display (not shown) to transfer the visuals of the path of the endotracheal tube, larynx, trachea or airway from the image sensor (161) to the display unit (30) or the external display.

The power button (32) is provided on any of the sides of the display unit (30). The power button (32) is within the range of the clinician's fingers. In the present aspect of the invention, the power button (32) is arranged at the bottom left of the display unit (30). The power button (32) is used to power on or power off the display screen (34). Specifically, the power button (32) is pressed and released to power on the display screen (34), and the power button (32) is pressed and held for 3-4 seconds to power off the display screen (34). A person skilled in the art can configure the duration for holding the power button (32) to power off the display screen (34).

In another aspect of the invention, the display screen (34) starts displaying the visuals of the path of the endotracheal tube once the display unit (30) is attached to the handle (10) and the display screen (34) is powered ON using the power button (32). The display screen (34) automatically starts displaying the visual of the endotracheal tube without pressing the record button (29).

In one more aspect of the invention, the video laryngoscope (100) is adapted to start displaying the visuals on the display screen (34) even if the display unit (30) is not attached to the handle (10). The display screen (34) displays the visuals by establishing the wireless connection between the handle (10) and the display unit (30).

Further, the output port (33) is provided on any of the sides of the display unit (30) to connect the display unit (30) to an external display (not shown) to show the visuals of the path of the endotracheal tube. The external display has a bigger screen size than the display screen (34) of the display unit (30). It is obvious to a person skilled in the art to provide a plurality of output ports on the display unit (30).

The display screen (34) of the display unit (30) is adapted to show visuals of the path of the endotracheal tube received from the image sensor (161). In the present aspect of the invention, the display unit (30) has a rectangular shape to accommodate the display screen (34). The display screen (34) has a size of 3.5 inches to provide better visibility from all angles. It is obvious to a person skilled in the art to increase the size of the display screen (34) according to the requirement.

Further, the touch user interface is provided to allow the clinician to interact with the video laryngoscope (100). The touch user interface of the display screen (34) is adapted to review and manage previously recorded images or videos which are stored in the memory of the display unit (30). The touch user interface includes a home page to show the current time and date, a menu icon to access the plurality of icons, and a battery icon to indicate the level of the battery. The display screen (34) is powered on using the power button (32) to display the home page. The clinician interacts with the menu icon of the home page by touching the menu icon displayed on the display screen (34) to access the plurality of the icons. The menu icon is provided on the bottom left corner of the display screen (34) to allow the clinician to reach the menu icon with one hand. After touching the menu icon, the processor receives the touch input from the touch user interface and processes the command to show the plurality of icons on the display screen (34).

The plurality of icons is assigned with specific actions to perform after receiving the command from the processor of the display unit (30). Specifically, the plurality of icons includes a settings icon to make changes in the brightness of the display screen (34), the volume of the sound, turn on or turn off the output port (33), and the like. Further, the plurality of icons includes a photo icon to view and manage previously recorded images, and a video icon to view and manage previously recorded videos. In another aspect of the invention, the plurality of icons includes a folder icon to view and manage the previously recorded images and videos in one place. A person skilled in the art can add more icons to the plurality of the icons to provide additional features and functions.

The touch user interface is adapted to show an indication of the captured image on the display screen (34) when the record button (29) is pressed by the clinician to capture the image. Further, the touch user interface is adapted to show a timer of the recording on the display screen (34) when the record button (29) is pressed and held to record the video. Further, the timer disappears from the display screen (34) after pressing the record button (29) to stop the recording.

In another aspect of the present invention, the display unit (30) includes a charging light (35) to indicate the charging status of the battery. The charging light (35) turns on when the battery is connected to a power source to recharge the battery, and turns off when the battery is not connected to the power source for recharging. It is obvious to a person skilled in the art to arrange the charging light (35) in any of the corners of the display unit (30).

Figure 11:
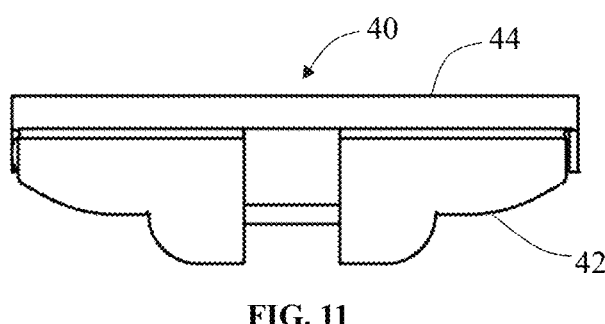
FIG. 11 illustrates a bottom view of a display cover of the video laryngoscope in accordance with the present invention.

Referring now to FIGS. 1, 10 and 11, a display cover (40) is provided to prevent the display unit (30) and the attachment assembly (25) from getting infected during the intubation process. The display cover (40) is made up of a transparent material to allow the clinician to view the display screen (34) without any hindrance. The display cover (40) includes a lower panel (42) and an upper panel (44) hinged at a hinge point. The lower panel (42) and the upper panel (44) pivot around the hinge point to cover the display unit (30). The upper panel (44) and the lower panel (42) of the display cover (40) are pressed to snap fit with each other after placing the display unit (30) within a cavity of the display cover (40). Further, the upper panel (44) has a flexible sheath (not shown) extending from the free end of the upper panel (44) to cover the attachment assembly (25) and a portion of the handle (10). The display cover (40) is disposable and can be disposed of once the intubation process is finished.

Referring again to FIGS. 1, and 2, the handle (10) is adapted to receive the blade (20) from the lower end (102) of the handle (10). The blade (20) is received around the outer surface of the handle (10) to entirely cover the handle (10) and the camera channel (15). The blade (20) is attached to the handle (10) while performing the intubation process. The handle is adapted to receive all types of blades like Macintosh, and Miller. Further, the handle (10) is adapted to receive both adult blades and child blades. The camera channel (15) is adapted to receive all types of blades like Macintosh, and Miller for both adults and children. The handle (10) does not require any other adjustments or mountings to receive adult blades and child blades. The blade (20) is slidable over the camera channel (15) to attach with the handle (10) to perform the intubation process. The blade (20) is detachably attached to the handle (10) and is detachable from the handle (10) after the intubation process.

In the present aspect of the invention, the blade (20) is attachable to the handle (10) through a dual ball mechanism (21) of the handle (10). The dual ball mechanism (21) includes two ball projections (211a, 211b) arranged opposite to each other to securely attach and detach the blade (20) to the handle (10). The two ball projections (211a, 211b) are biased to radially extend away from the centre axis of the handle (10). The two ball projections (211a, 211b) engage with the blade (20). Specifically, the blade (20) has two openings (not shown) to engage with two ball projections (211a, 211b) of the handle (10) to securely hold the blade (20) thereover. The blade (20) has a first cavity (256) formed within the blade (20). The first cavity (256) is having a shape that is adapted to fit over the handle (10) and cover the handle (10) during the intubation process. The first cavity (256) allows the blade (20) to accommodate the handle (10) and remain firm in place during the intubation process. Further, the blade (20) has a second cavity (257) formed at a tongue portion (253) of the blade (20). The second cavity (257) is configured to accommodate the camera channel (15) and the camera housing (16) therein. The second cavity (257) accommodates the camera channel (15), which runs along the length of the tongue portion (253). The second cavity (257) provides space for the camera channel (15) to be housed within the blade (20).

The two ball projections (211a, 211b) ensure that the blade (20) is held in place until the two ball projections (211a, 211b) are pressed to detach the blade (20). The blade (20) is disposed of after detaching from the handle (10) to reduce the chance of infection and cross-contamination. Disposing of the blade (20) after one use allows the video laryngoscope (100) to control the spread of infection which can be spread by using the same blade again and again.

Further, the blade (20) has an opening (165) to allow the image sensor (161) and the light source (162) to capture the visuals of the path of the endotracheal tube. The image sensor (161) captures the visuals of the path of the endotracheal tube, larynx, trachea or airway and transfers the visuals to the display unit (30).

Before performing the intubation process, the clinicians attach the blade (20) to the handle (10). The blade (20) can be an adult blade or a child blade. The blade (20) is slidable over the camera channel (15) and is attached to the handle (10) through the dual ball mechanism (21) of the handle (10). Further, the display unit (30) is placed inside the lower panel (42) of the display cover (40) and the upper panel (44) is pivoted to close the display cover (40). The flexible sheath is wrapped around the attachment assembly (25) and the portion of the handle (10). Once the flexible sheath is wrapped, the video laryngoscope (100) is ready to use for the intubation process. The display unit (30) is rotated to configure the position according to the clinician's requirement. The movement of the display unit (30) is facilitated by the hinge (26).

While performing the intubation process, the power button (32) is pressed to activate the display screen (34), the image sensor (161), and the light source (162). The visuals of the path of the endotracheal tube and the airway are displayed on the display screen (34). The deflector (18) of the camera housing (16) reduces the scattering of the light from the light source (162). The deflector (18) helps to reduce the distortion and blurriness of the images. Further, the record button (29) is provided to capture the image and record the video. The record button (29) is pressed and released to capture the image, and the record button (29) is pressed and held for 2 to 3 seconds to record the video. The video laryngoscope (100) is completely covered from the outside eliminating the risk of the video laryngoscope (100) getting infected. After the intubation process, the display cover (40) is removed from the display unit (30) and disposed of to avoid spreading infection. Further, the blade (20) is removed from the handle (10). The blade (20) which is mainly in contact with the body parts is disposed of after one use which helps to reduce the rate of infection or cross-contamination spread due to the repetitive use of the blade (20).

Further, the video laryngoscope (100) allows the clinician to have one hand free while operating the video laryngoscope (100) during the intubation process. In an operating room, clinicians need free hands to simultaneously use multiple devices or perform multiple actions. With the placement of the power button (32) at the bottom left of the display unit (30), the menu icon on the bottom left of the display screen (34) and the record button (29) under the display unit (30), the clinician can fully operate the video laryngoscope (100) with their left hand thus leaving the right hand free.

In another aspect of the present invention, the video laryngoscope (100) includes a handle (10), a blade (20), and a display unit (30). The display unit (30) is attached to the handle (10) without using an attachment assembly (25). Specifically, the display unit (30) includes an attaching element (not shown) extending from a bottom portion of the display unit (30) to attach with the handle (10). It is obvious to a person skilled in the art to configure the attaching element of the display unit (30) to provide a threaded attachment or a snap-fit attachment or a similar attachment, to ensure a secure and functional connection between the display unit (30) and the handle (10).

Therefore, the present invention has the advantage of providing the video laryngoscope (100) to perform the intubation process. The video laryngoscope (100) is provided with the display unit (30) which rotates and moves in the back-and-forth direction to increase the visibility for the clinician. Further, the handle (10) of the video laryngoscope (100) is adapted to receive the adult blades as well as child blades, which reduces the other requirements like different handles for different blades or mountings to receive the different types of blades on the same handle (10). Further, the deflector (18) reduces the distortion and blurriness of the images for better quality visualisation. Furthermore, the handle (10) is covered by the blade (20) and the display unit (30) is covered by the display cover (40) which completely covers the video laryngoscope (100) and prevents the video laryngoscope (100) from getting infected during the intubation process.

The foregoing descriptions of specific embodiments of the present invention have been presented for purposes of illustration and description. They are not intended to be exhaustive or to limit the present invention to the precise forms disclosed, and obviously, many modifications and variations are possible in light of the above teaching. The embodiments were chosen and described in order to explain the principles of the present invention best and its practical application, to thereby enable others skilled in the art to best utilise the present invention and various embodiments with various modifications as are suited to the particular use contemplated. It is understood that various omission and substitutions of equivalents are contemplated as circumstance may suggest or render expedient, but such are intended to cover the application or implementation without departing from the scope of the claims of the present invention.

I claim:

1. A video laryngoscope (100), comprising:
a handle (10) having an upper end (101) and a lower end (102), the upper end (101) is adapted to receive a display unit (30) therein, the handle (10) is adapted to receive a blade (20) for the intubation process;
a camera channel (15) extending from the lower end (102) of the handle (10), the camera channel (15) is a flexible link having a first end connected to the handle (10) and a second end comprising a camera housing (16), wherein the camera housing (16) includes:
an image sensor (161) arranged within the camera housing (16) facing outwardly to capture visuals of the path of an endotracheal tube, larynx, trachea, or airway; a light source (162) arranged adjacent to the image sensor (161) within the camera housing (16) to illuminate the path of the endotracheal tube and the airway;
a deflector (18) mountable on the camera housing (16), between the image sensor (161) and the light source (162), wherein the deflector (18) is a rectangular strip made up of silicone material attachable on an outer surface of the camera housing (16), in between the image sensor (161) and the light source (162) to minimize light scatter and direct light exposure to the image sensor (161) from the light source (162).

2. The video laryngoscope (100) as claimed in claim 1, wherein the camera housing (16) is a rectangular box having a front portion (1601) and a back portion (1602), the back portion (1602) is configured to attach the camera housing (16) to the camera channel (15) and the front portion (1601) is adapted to accommodate the image sensor (161), the light source (162), and the deflector (18) positioned to face outward for capturing visuals of the path of an endotracheal tube, larynx, trachea, or airway.

3. The video laryngoscope (100) as claimed in claim 2, wherein the front portion (1601) of the camera housing (16) has an image sensor opening (1611) and a light source opening (1621) adapted to expose the image sensor (161) and the light source (162) respectively allowing the capturing of the visuals of the path of an endotracheal tube, larynx, trachea, or airway.

4. The video laryngoscope (100) as claimed in claim 3, wherein the camera housing (16) has a first compartment (1603) and a second compartment (1604) arranged at the front portion (1601) within the camera housing (16) corresponding to the image sensor opening (1611) and the light source opening (1621) respectively, the first compartment (1603) is adapted to receive and hold the image sensor (161) within the camera housing (16) facing outward through the image sensor opening (1611) and the second compartment (1604) arranged adjacent to the first compartment (1603) to receive and hold the light source (162) within the camera housing (16) facing outward through the light source opening (1621).

5. The video laryngoscope (100) as claimed in claim 1, wherein the deflector (18) includes a rectangular portion (181), and a plurality of legs (182) extending from distal ends of the rectangular portion (181) to be mounted on the camera housing (16).

6. The video laryngoscope (100) as claimed in claim 5, wherein the plurality of legs (182) is provided with respective locking elements (1821a, 1821b) to attach the deflector (18) to the camera housing (16), wherein the camera housing (16) has a plurality of openings (1682) to receive the corresponding plurality of legs (182) of the deflector (18) to securely hold the deflector (18) on the camera housing (16).

7. The video laryngoscope (100) as claimed in claim 6, wherein the plurality of openings (1682) is configured in between the image sensor opening (1611) and the light source opening (1621) to receive the deflector (18), separating the image sensor (161) and the light source (162) to minimize light scatter and direct light exposure to the image sensor (161).

8. The video laryngoscope (100) as claimed in claim 1, wherein the deflector (18) is an extruded portion, extending integrally from an outer surface of the camera housing (16), the extruded portion extends from the outer surface in such a way that an image sensor opening (1611) and a light source opening (1621) are separated from each other to avoid direct light exposure to the image sensor (161) from the light source (162).

9. The video laryngoscope (100) as claimed in claim 1, wherein the blade (20) is adapted to receive the camera channel (15) and the camera housing (16) within a second cavity (257) of the blade (20) when attached to the handle (10).

10. The video laryngoscope (100) as claimed in claim 1, wherein the camera channel (15) is the flexible link extending from a tapered portion (14) of the handle (10) and comprises an electric circuit to transfer the visuals like images and videos from the image sensor (161) to the display unit (30).

11. A camera channel (15) for a handle (10) of a video laryngoscope (100), the camera channel (15) comprising:
a camera housing (16) arranged at a distal end of the camera channel (15); wherein, the camera housing (16) includes:
an image sensor (161) and a light source (162) arranged adjacent to each other;
a deflector (18) mounted between the image sensor (161) and the light source (162), the deflector (18) has a rectangular portion (181) and a plurality of legs (182) extending from the rectangular portion (181) to mount the deflector (18) on the camera housing (16), the plurality of legs (182) is provided with respective locking elements (1821a, 1821b) configured to lock the plurality of legs (182) in a corresponding plurality of openings (1682) of the camera housing (16) to securely hold the deflector (18) on the camera housing (16), wherein the plurality of openings (1682) is configured in between an image sensor opening (1611) and a light source opening (1621) to receive the deflector (18), separating the image sensor (161) and the light source (162) to minimize light scatter and direct light exposure to the image sensor (161).

* * * * *